United States Patent
Wang et al.

(10) Patent No.: US 12,091,414 B2
(45) Date of Patent: Sep. 17, 2024

(54) CRYSTALLINE FORM OF DI-P-TOLUOYL-L-TARTRATE OF UPADACITINIB

(71) Applicant: SUZHOU PENGXU PHARMATECH CO., LTD., Suzhou (CN)

(72) Inventors: Peng Wang, Suzhou (CN); Pixu Li, Suzhou (CN); Qiang Wei, Suzhou (CN); Wen Cheng, Suzhou (CN)

(73) Assignee: SUZHOU PENGXU PHARMATECH CO., LTD., Suzhou (CN)

( * ) Notice: Subject to any disclaimer, the term of this patent is extended or adjusted under 35 U.S.C. 154(b) by 676 days.

(21) Appl. No.: 17/427,357

(22) PCT Filed: May 8, 2020

(86) PCT No.: PCT/CN2020/089119
§ 371 (c)(1),
(2) Date: Jul. 30, 2021

(87) PCT Pub. No.: WO2020/224633
PCT Pub. Date: Nov. 12, 2020

(65) Prior Publication Data
US 2022/0041611 A1   Feb. 10, 2022

(30) Foreign Application Priority Data
May 9, 2019   (CN) .......................... 201910385804.0

(51) Int. Cl.
C07D 487/14   (2006.01)

(52) U.S. Cl.
CPC ........ *C07D 487/14* (2013.01); *C07B 2200/13* (2013.01)

(58) Field of Classification Search
None
See application file for complete search history.

(56) References Cited

FOREIGN PATENT DOCUMENTS

| CN | 108368121 A | 8/2018 | |
| WO | WO-2017066775 A1 * | 4/2017 | ......... A61K 31/4985 |
| WO | 2020063939 A1 | 4/2020 | |

OTHER PUBLICATIONS

Atipamula et al., Cryst. Growth Des. 2012, 12, 5, 2147-2152 (Year: 2012).*
Aceto et al., Journal of Medicinal Chemistry 1979 22 (2), 174-177 (Year: 1979).*
International Application No. PCT/CN2020/089119, International Search Report and Written Opinion mailed Aug. 7, 2020, 12 pages.
European Application No. 20803029.6, Extended European Search Report mailed Mar. 31, 2022, 5 pages.

* cited by examiner

*Primary Examiner* — Jeffrey S Lundgren
*Assistant Examiner* — Anthony Joseph Seitz
(74) *Attorney, Agent, or Firm* — MagStone Law, LLP; Enshan Hong

(57) ABSTRACT

The present application provides a upadacitinib salt compound and a preparation method therefor. The salt involved in the method in the present application has an easy preparation operation, a cheap raw material easy to get, and a good purification effect on upadacitinib, and is beneficial to industrial production.

2 Claims, 2 Drawing Sheets

CRYSTALLINE FORM OF DI-P-TOLUOYL-L-TARTRATE OF UPADACITINIB

CROSS REFERENCE TO RELATED APPLICATION

This is a U.S. national stage of international application No. PCT/CN2020/089119 filed on May 8, 2020, which claims the benefit of China Patent Application No. 201910385804.0 filed on May 9, 20219, the disclosure of which is incorporated herein by reference in its entirety.

BACKGROUND OF THE INVENTION

1. Technical Field of the Invention

This application is related to the synthesis of drug, in particular to upadacitinib salt and preparation method thereof.

2. Background of the Invention

The specific causes of rheumatoid arthritis (RA) and psoriatic arthritis (PsA) are unknown, and it is presumed from medical practice that there is an important relationship between RA and the partial defects of the patient's immune function.

Rheumatoid arthritis has a long disease course, and associated immune dysfunction, patients often die from complications, such as cardiovascular diseases, infections and renal function impairment.

Currently, JAK inhibitors are one of the effective treatments for such immune system diseases. Among them, upadacitinib, an innovative new drug of AbbVie for the treatment of rheumatoid arthritis and psoriatic arthritis, is a new target JAK1 inhibitor. JAK1 is a kinase, which plays a key role in the pathophysiologic processes of various inflammatory diseases including rheumatoid arthritis (RA), Crohn's disease (CD), ulcerative colitis (UC), psoriatic arthritis (PsA), etc. Currently, AbbVie is also evaluating the potential effectiveness of upadacitinib for other immune diseases, including PsA, ankylosing spondylitis (AS) and atopic dermatitis.

So far, there are few related patents of upadacitinib. The main patent route is a synthetic route of the original innovator AbbVie (WO2017066775A1), which reports hydrochloride, tartrate, maleate and other salts.

The polymorphic form of a compound refers to the existence of two or more different crystalline forms in the compound. Polymorphism exists extensively in organic compounds. There are significant differences in solubility, melting point, density, stability, etc. for the different crystalline forms of the same compound, which affect the stability and uniformity of the compound in different degrees. Different crystalline forms have obvious differences in the purification ability of the compound through crystallization in the purification process of the compound. Therefore, comprehensive and systematic polymorphic screening and selection of the most suitable crystalline form are one of the important nonnegligible contents of the research and development of pharmaceutical processes.

The effective control of impurities is very important in the drug production, which is of great significance to ensure drug quality. For being responsible to patients, the R&D of pharmaceutical companies should pay close attention to impurity control. The research on the salt form, crystal form and purification process of pharmaceutical intermediate compounds is conducive to controlling the quality of APIs, thereby ensuring the quality and safety of medicines.

SUMMARY OF THE INVENTION

The present application provides several new salt forms and crystal forms of upadacitinib. The new crystal forms disclosed in this application have favorable properties, such as good stability, easy handling, developable process, lower cost etc., which are of important value for the optimization and development of the drug in the future. Its outstanding advantage is that the impurities produced in the synthesis process can be effectively purified through this salt-forming process.

The object of the invention is to provide the salt form of upadacitinib compound I and the corresponding crystal form. One crystal form of upadacitinib Di-p-toluoyl-L-tartrate salt is named as crystal Form A, which is characterized by X-ray powder diffraction ("XRPD"), Differential Scanning Calorimetry ("DSC"), thermogravimetric analysis ("TGA") and the processes for their preparation.

The present invention provides crystalline Form A of upadacitinib Di-p-toluoyl-L-tartrate characterized by a XRPD pattern depicted in FIG. 1 comprising peaks at 2-theta angles of about 3.9°±0.2°, 7.5°±0.2°, 7.7°±0.2°, 10.4°±0.2°, 15.2°±0.2°, and 23.4°±0.2°.

In addition, the corresponding salts formed by upadacitinib, oxalic acid and p-toluenesulfonic acid also have better purification effects. Compound I can also form corresponding salts with camphorsulfonic acid, benzoic acid, malic acid, citric acid, phosphoric acid, acetic acid, propionic acid, gluconic acid, malonic acid, succinic acid, methylmalonic acid, stearic acid, palmitic acid, fumaric acid Acids, etc.

The present invention further provides a process for preparing crystalline upadacitinib salt by crystallization process with corresponding acid and solvent.

Furthermore, the crystallization process includes suspension stirring, heating and cooling, volatilization or countercurrent solvent.

Furthermore, the solvent includes a single or mixed system of water, alcohols, ethers, ketones, esters, aromatic hydrocarbons, halogenated hydrocarbons, nitriles, nitroalkanes, and aliphatic hydrocarbon solvents.

Another object of the application is to provide the use of compound I and its corresponding p-toluenesulfonate, oxalate, and Di-p-toluoyl-L-tartrate for synthesis and preparation of the immune system drug upadacitinib.

The beneficial effects of the application are:

The salt form and crystal form provided by the present invention have better stability;

Compared with the upadacitinib tartrate salt disclosed in the literature, the crystallization method provided by the application can effectively improve the purity of the drug compound and effectively reduce the impurity content;

The preparation method of the new crystal form provided by the present invention is simple, good repeatable, controllable, and is suitable for industrial production.

DESCRIPTION OF PREFERRED EMBODIMENTS

Figure 1:
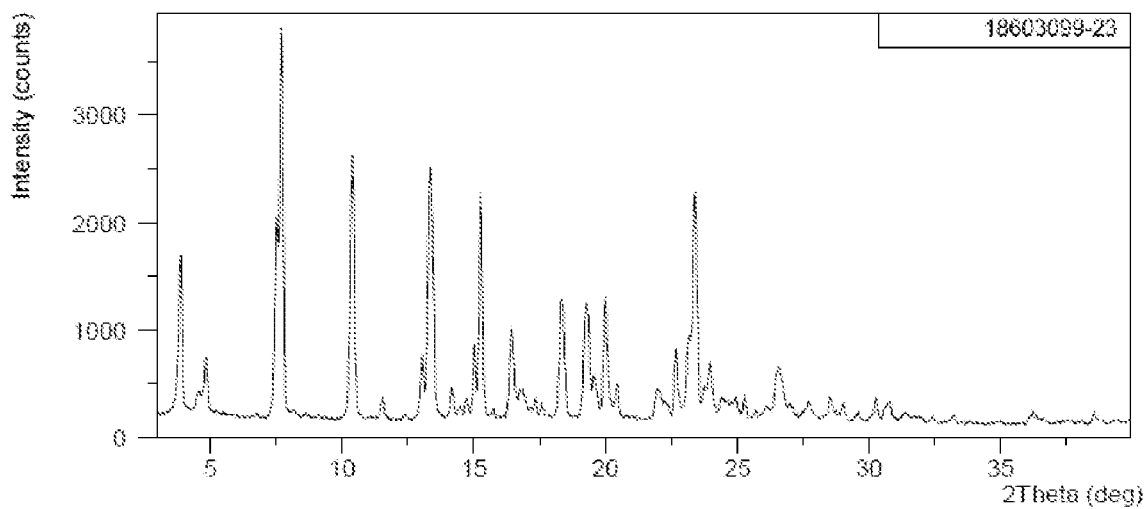
FIG. 1 is the XRPD image of Di-p-toluoyl-L-tartrate crystal form A of compound I.
Figure 2:
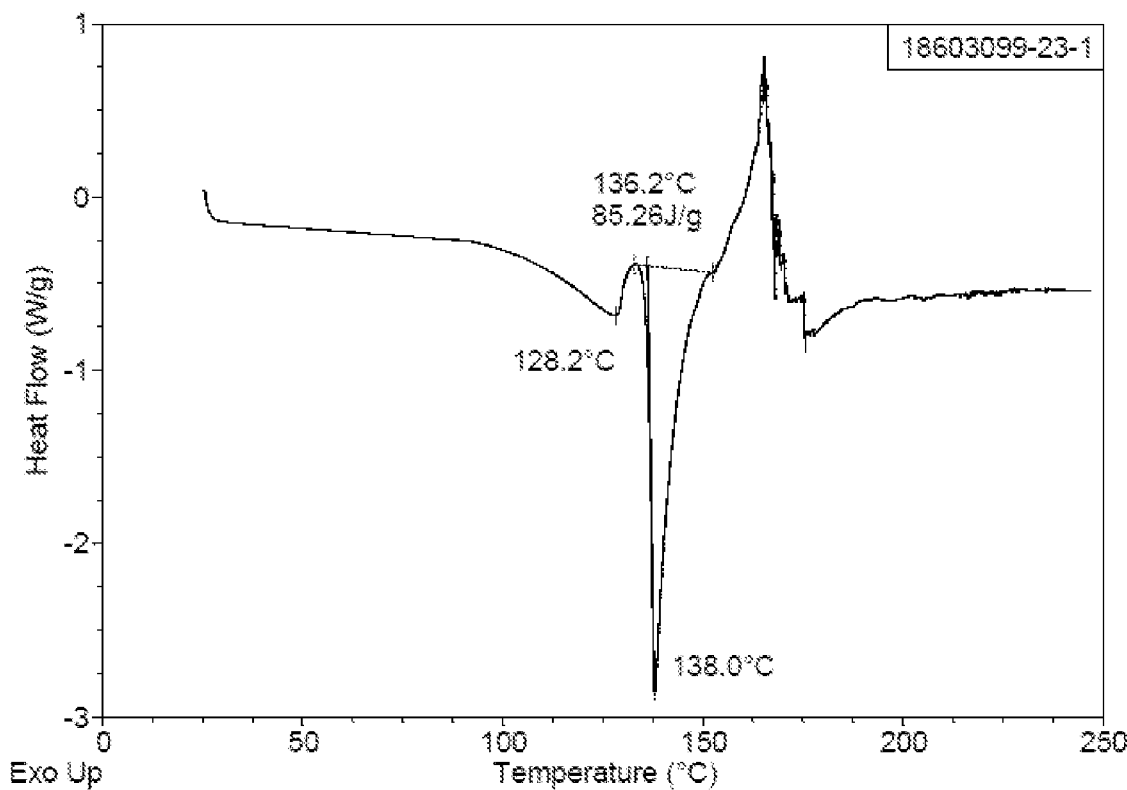
FIG. 2 is a DSC chart of Di-p-toluoyl-L-tartrate crystal form A of compound I.
Figure 3:
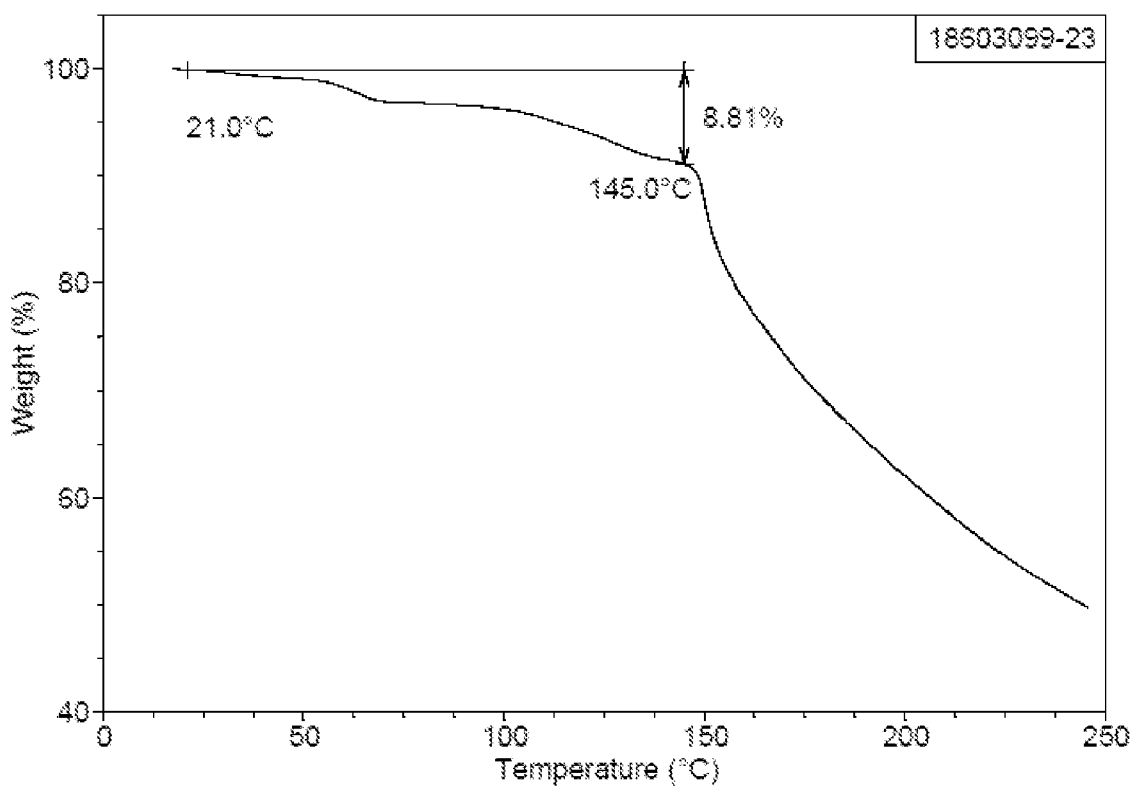
FIG. 3 is a TGA chart of Di-p-toluoyl-L-tartrate crystal form A of compound I.
Figure 4:
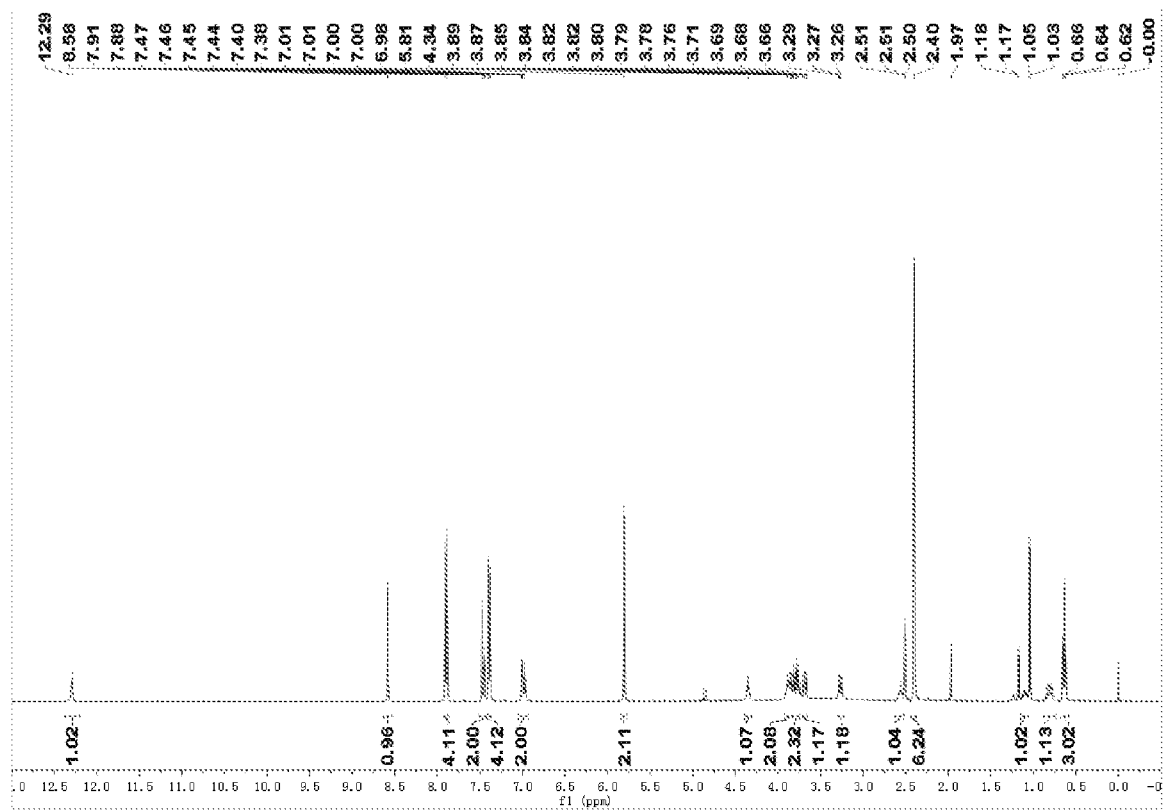
FIG. 4 is an HNMR chart of Di-p-toluoyl-L-tartrate crystal form A of compound I.

The present disclosure is further explained by below specific embodiments, but it should not be concluded to limit the protective scope of the present disclosure. Those skilled in the art can make improvements on the preparation method and use of instruments within the scope of the claims. These improvements should also be considered as within the protection scope of the present disclosure. Therefore, the protection scope of the invention should be subject to the appended claims.

In the following embodiments, the test method is usually implemented according to conventional conditions or conditions recommended by the manufacturer; the compound I is prepared by the method of patent WO2017066775.

The explanations of the abbreviations used in the present disclosure are as follows:
XRPD: X-ray powder diffraction
DSC: Differential Scanning calorimetry
TGA: Thermogravimetric Analysis The X-ray powder diffraction pattern of the present invention is collected on the D2PHASER X-ray powder diffractometer of Bruker Company.

The XRPD method parameters of the present invention are as follows:

| | |
|---|---|
| Step Size [°2Th.]: 0.0201 | Scan Step Time [s]: 0.1 |
| K-Alpha1 [Å]: 1.54060 | K-Alpha2 [Å]: 1.54439 |
| Generator Settings: 10 mA, 30 kV | Scan Range [°2Th.]: 3-40 |

The differential scanning calorimetry (DSC) chart of the present invention is collected on a differential scanning calorimeter DSC2000 from TA Instruments.

The method parameters of the differential scanning calorimetry (DSC) of the present invention are as follows:

| | |
|---|---|
| Sample tray | Aluminum plate, gland |
| Temperature range/° C. | RT-250 |
| Scanning rate/° C./min | 10 |
| Protective gas | Nitrogen |

The thermo-gravimetric analysis (TGA) graph of the present invention is collected on the TGA Q500 of TA Instruments' thermogravimetric analyzer. The method parameters of the thermo-gravimetric analysis (TGA) of the present invention are as follows:

| | |
|---|---|
| Sample tray | Aluminum plate, gland |
| Temperature range/° C. | RT-250 |
| Scanning rate/° C./min | 10 |
| Protective gas | Nitrogen |

The high-performance liquid chromatography (HPLC) results of the present invention are collected on Waters 2695. The method parameters of the high-performance liquid chromatography (HPLC) of the present invention are as follows:
Liquid chromatography column: Agilent Zorbax Plus-C18, 4.6*100 mm, 3.5 um;
Mobile phase: water-acetonitrile-trifluoroacetic acid system;
Flow rate: 1 mL/min;
Column temperature: 40° C.;
Detection wavelength: 220 nm.

Example 1

Preparation Method of Compound I Oxalate:

380 mg of compound I was dissolved in 6 mL of isopropyl acetate, and 100 mg/2 mL of oxalic acid in isopropyl acetate was slowly added dropwise at 20° C., stirred at room temperature for 2 h, filtered, and sampled to test. The purity by HPLC was 99.51%.

Example 2

Preparation Method of p-Toluenesulfonic Acid Salt of Compound I:

380 mg of compound I was dissolved in 6 mL of isopropyl acetate, 360 mg/2 mL of p-toluenesulfonic acid in isopropyl acetate was slowly added dropwise at 20° C., stirred at room temperature for 2 hours, filtered, and sampled for test. The purity by HPLC was 98.73%.

Example 3

The Preparation Method of Compound I Di-p-toluoyl-L-tartrate:

Dissolve 380 mg of compound I in 6 mL of isopropyl acetate, slowly add 390 mg/2 mL of Di-p-toluoyl-L-tartaric acid in isopropyl acetate solution dropwise at 20 C, stir at room temperature for 2 h, filter, and sampled for test. The purity by HPLC was 99.32%.

Example 4 (Summary of Comparison Results)

Comparison of the Salt-Forming Purification Effect of Compound I:

| Entry | Acid | HPLC |
|---|---|---|
| 18603097-0 | Free base (starting material for salt formation) | 84.58% |
| 18603097-22 | oxalic acid | 99.51% |
| 18603097-23 | p-Toluenesulfonic acid | 98.73% |
| 18603097-24 | Di-p-toluoyl-L-tartaric acid | 99.32% |
| 18603099-24 | L-tartaric acid | 93.49% |

Example 5

Preparation Method of Di-p-toluoyl-L-tartrate Crystal Form A of Compound I:

Dissolve 390 mg of compound I in a mixed solution of 1 mL of isopropyl acetate, 0.5 mL of isopropanol and 0.3 mL of water, and slowly drop 400 mg/2 mL of Di-p-toluoyl-L-tartaric acid at 50° C. The isopropyl acetate solution was stirred at 50° C. for 2 hours, and then 5 mL of isopropyl acetate solution was added to slowly reduce to room temperature, filtered and drained 740 mg of solid. The HPLC purity of the sample was 99.78%.

HNMR data:

1H-NMR (DMSO-d6, 400 MHz) δ: 12.29 (1H, s), 8.58 (1H, s), 7.89 (4H, d), 7.40-7.60 (2H, m), 7.38 (4H, d), 6.95-7.06 (2H, m), 5.81 (2H, s), 4.35 (1H, dd), 5.65-5.93 (5H, m), 3.27 (1H, dd), 2.50-2.62 (1H, m), 2.40 (6H), S), 1.05-1.15 (1H, m), 0.75-0.88 (1H, m), 0.64 (3H, t).

The test XRPD results are as follows:

| 2theta | d value | Intensity % |
|---|---|---|
| 3.88 | 22.80 | 41.36 |
| 7.47 | 11.83 | 33.28 |
| 7.70 | 11.48 | 100.00 |
| 10.40 | 8.50 | 62.44 |
| 13.03 | 6.80 | 22.55 |
| 13.40 | 6.61 | 79.74 |
| 15.26 | 5.81 | 40.57 |
| 16.46 | 5.39 | 24.26 |
| 18.40 | 4.82 | 32.10 |
| 19.32 | 4.60 | 46.82 |
| 19.98 | 4.44 | 49.06 |
| 23.13 | 3.85 | 25.62 |
| 23.44 | 3.79 | 42.78 |
| 23.96 | 3.71 | 24.54 |

Example 6

Preparation Method of Di-p-toluoyl-L-tartrate Crystal Form A of Compound I:

Add 415 mg of compound I and 430 mg of Di-p-toluoyl-L-tartaric acid into the reaction flask, add a mixed solution of 8 mL isopropyl acetate, 0.5 mL isopropanol and 0.3 mL water, and stir at 50° C. for 2 hours, It was cooled to room temperature slowly, filtered and drained 755 mg of solid, and the HPLC purity of the sample was 99.79%.

HNMR data:

1H-NMR (DMSO-d6, 400 MHz) δ: 12.29 (1H, s), 8.58 (1H, s), 7.89 (4H, d), 7.40-7.60 (2H, m), 7.38 (4H, d), 6.95-7.06 (2H, m), 5.81 (2H, s), 4.35 (1H, dd), 5.65-5.93 (5H, m), 3.27 (1H, dd), 2.50-2.62 (1H, m), 2.40 (6H), S), 1.05-1.15 (1H, m), 0.75-0.88 (1H, m), 0.64 (3H, t).

The Test XRPD Results are as Follows:

| 2theta | d value | Intensity % |
|---|---|---|
| 3.87 | 22.81 | 43.59 |
| 7.48 | 11.82 | 52.26 |
| 7.69 | 11.50 | 100.00 |
| 10.37 | 8.53 | 70.43 |
| 13.28 | 6.66 | 60.79 |
| 15.00 | 5.91 | 20.68 |
| 15.24 | 5.81 | 60.49 |
| 16.39 | 5.41 | 24.30 |
| 18.27 | 4.86 | 30.15 |
| 19.21 | 4.62 | 28.37 |
| 19.97 | 4.45 | 32.89 |
| 23.12 | 3.85 | 22.23 |
| 23.36 | 3.81 | 58.03 |

The invention claimed is:

1. Crystalline Form A of Di-p-toluoyl-L-tartrate of a compound of formula I:

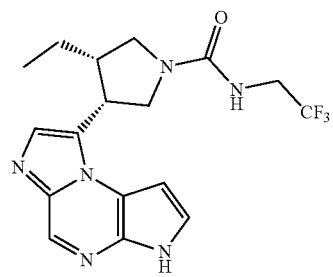

characterized by a X-ray powder diffraction pattern comprising peaks at 3.9, 7.5, 10.4, 13.4, 15.2, and 23.4°±0.2 2θ degrees.

2. A pharmaceutical composition comprising the di-p-toluoyl-L-tartrate of claim 1.

* * * * *